United States Patent [19]

Chatterjie et al.

[11] 4,089,855

[45] May 16, 1978

[54] PROCESS FOR THE STEREOSELECTIVE REDUCTION OF 6- AND 8-KETO MORPHINE AND MORPHINAN DERIVATIVES WITH FORMAMIDINESULFINIC ACID AND COMPOUNDS OBTAINED THEREBY

[75] Inventors: Nithiananda Chatterjie, Flushing; Charles E. Inturrisi, New York, both of N.Y.

[73] Assignee: Cornell Research Foundation, Inc., Ithaca, N.Y.

[21] Appl. No.: 679,677

[22] Filed: Apr. 23, 1976

[51] Int. Cl.$^2$ .................. C07D 489/08; A61K 31/485
[52] U.S. Cl. ...................................... 260/285; 424/260
[58] Field of Search ......................................... 260/285

[56] References Cited

U.S. PATENT DOCUMENTS 2,774,762  12/1956  Baizer .................................. 260/285

FOREIGN PATENT DOCUMENTS 6,516,548   7/1965   Japan.
6,522,189  10/1965   Japan.

OTHER PUBLICATIONS

Chatterjie et al., J. Med. Chem., 18(5) pp. 490–492, 5/75.
Herz et al., J. Chem. Soc., Perkin Trans I(22) pp. 2633–2634 (1973).
Rüll, Bull. Soc. Chimique de France, 1962, pp. 1337–1340 (1962).
Makleit et al., Chemical Abstracts, v. 72, 121,745(s) (1970).
Cone, Chemical Abstracts, vol. 80, 10207p (1974).
Chatterjie et al., Durg Metab. Dispos., 1974, pp. 401–405.

*Primary Examiner*—Donald G. Daus
*Assistant Examiner*—Diana G. Rivers
*Attorney, Agent, or Firm*—Bacon & Thomas

[57] ABSTRACT

Process for the stereoselective synthesis of 6$\beta$- and 8$\beta$-hydroxy epimers by the chemical reduction of 6- and 8-keto derivatives in the morphine and morphinan series utilizing alkaline formamidinesulficic acid. The 6$\beta$- and 8$\beta$-hydroxy derivatives obtained according to the invention evidence narcotic antagonist and/or agonist activity and are also useful in the chemical and pharmacological standardization of various morphine and codeine derivatives and metabolites.

18 Claims, No Drawings

PROCESS FOR THE STEREOSELECTIVE REDUCTION OF 6- AND 8-KETO MORPHINE AND MORPHINAN DERIVATIVES WITH FORMAMIDINESULFINIC ACID AND COMPOUNDS OBTAINED THEREBY

This invention was made with the grant support of the Department of Health, Education and Welfare.

BACKGROUND OF THE INVENTION

The present invention relates to a process for the stereoselective reduction of 6- and 8-keto phenanthrene derivatives including N-substituted derivatives, employing an alkaline solution of formamidinesulfinic acid to form the corresponding 6β- and 8β-hydroxy epimers thereof.

In recent years, there has been considerable interest in the development of narcotic antagonists capable of blocking the euphorigenic and addictive effects of narcotics. Exemplary of such compounds are cyclazocine, N-allylnoroxymorphone (naloxone), N-cyclopropylmethyl-noroxymorphone (naltrexone) and 3,14β-dihydroxy-N-cyclobutulmethylmorphinan (butorphanol). Various derivatives in the morphine and morphinan series have heretofore been prepared which display combined narcotic antagonist-analgetic (agonist) properties. See, for example, U.S. Pat. Nos. 3,393,197; 3,332,950; 3,814,768; 3,819,635; and 3,896,226. Such derivatives having combined antagonist-agonist properties are very desirable as replacements for pure morphine in analgesic applications.

As a consequence of the species variation with respect to narcotic antagonist-agonist activity and relative potencies of various compounds previously investigated, there has also been considerable interest in delineating the role of biotransformation and metabolites in observed activity for morphine derivatives as well as determination of receptor stereospecificity. Accordingly, synthetic methods for the preparation of 6-keto reduction products of the morphine nucleus compounds have heretofore been described.

For example, processes for the synthesis of 6α-hydroxy epimers of N-substituted 14-hydroxydihydronormorphinones are known utilizing a hydride reduction to form the 6α-hydroxy derivatives of N-substituted 14-hydroxydihydronormorphines (I. J. Pachter and Z. Matossian, U.S. Pat. No. 3,393,197 [1968]). However, no process for the selective obtainment of 6β epimeric morphine derivatives and especially from 6-keto morphine derivatives lacking the 14-hydroxy group have been described.

Although formamidinesulfinic acid has been used extensively for bleaching in the textile industry, few applications have been made of this reducing agent in preparative organic chemistry. Herz et al. have reported the reduction of certain 3- and 6-ketonic steroids (5α-chloestane 3-one) utilizing a strong alkaline solution of formamidinesulfinic acid as the reducing agent (Josef E. Herz and Lilia Albert de Marquez, J. Chem. Soc., 2633 [1973]). However, the authors also observed that regardless of whether the reducing agent was formamidinesulfinic acid, Na/alcohol or LiAlH₄, reduction yielded the same ratio of isomers (3β:3α) and that all three reagents favored equatorial alcohols (beta) in the chair conformation. The foregoing is clearly not the case with respect to 6-keto derivatives with the morphine skeleton, wherein it has been found that hydride reducing agents, for example, give predominantly 6α-OH products in which the hydroxy group is axial. Hydride reduction processes have resulted predominantly in the preparation of 6α-hydroxy morphine derivatives and such hydride reductions of compounds of this class have been generally totally ineffective in the stereoselective synthesis of 6β-hydroxy compounds. See, E. J. Cone, Tetrahedron Letters, 2607 (1973), E. J. Cone, C. W. Gorodetzky and S. Y. Yeh, Pharmacologist 16, 225 (1974) and U. Weiss and S. J. Daum, J. Med. Chem., 8, 123 (1965). Also, with respect to the borohydride reduction of dihydrocodeinone, see Rull, Bull, Soc. Chim. France, 1337 (1962).

SUMMARY OF THE INVENTION

Accordingly, it is a primary object of the present invention to provide a simple and effective process for the stereoselective reduction of 6- and 8-keto morphine and morphinan derivatives to the corresponding 6β- and 8β-hydroxy epimers thereof in high yield.

It is a further object of the invention to provide certain novel 6β- and 8β-hydroxy morphine and codeine derivatives.

In accomplishing the foregoing objects, there has been provided in accordance with the present invention a process wherein 6-keto compounds and 8-keto compounds in the morphine and morphinan series are stereoselectively reduced by employing an alkaline solution of formamidinesulfinic acid as the reducing agent to selectively obtain the corresponding 6β-hydroxy and 8β-hydroxy compounds.

Preferably, the process according to the invention comprises reducing with an alkaline solution of formamidinesulfinic acid a compound of the formula:

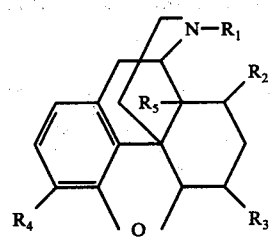

I or the formula:

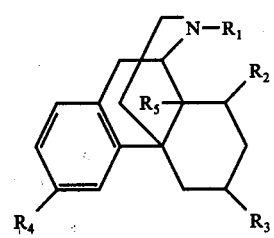

II wherein R₁ represents hydrogen, lower alkyl (e.g., methyl, ethyl, propyl, etc.), lower alkenyl (e.g., 1-propenyl), lower alkynyl, carbocyclic lower alkyl (e.g., cyclopropyl methyl, cyclobutylmethyl, etc.), lower alkyl ring-substituted carbocyclic lower alkyl (e.g., methylcyclopropyl methyl), cycloalkenyl, cycloalkenyl lower alkyl, furyl lower alkyl (e.g., furyl methyl), thiophenyl lower alkyl (e.g., thiophenyl methyl), pyridinyl lower alkyl (e.g., 2-pyridinyl methyl), piperidinyl lower alkyl (e.g., 2-piperidinyl methyl), or thiozolyl lower alkyl (e.g., 5-thiozolylmethyl);

$R_2$ and $R_3$ represents hydrogen and =O, or =O and hydrogen, respectively;

$R_4$ represents hydroxy, or lower alkoxy; and $R_5$ represents hydrogen, hydroxy or lower acyl, to produce the corresponding 6$\beta$- or 8$\beta$-hydroxy epimer.

In accordance with another aspect of the present invention there has been provided certain novel 6$\beta$- and 8$\beta$-hydroxy morphine derivatives. These compounds are defined by the formula:

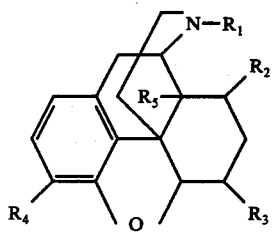

wherein $R_1$ represents hydrogen, lower alkyl (e.g., methyl, ethyl, propyl, etc.), lower alkenyl (e.g., 1-propenyl), lower alkynyl, carbocyclic lower alkyl (e.g, cyclopropyl methyl, cyclobutylmethyl, etc.), lower alkyl ring-substituted carbocyclic lower alkyl (e.g., methylcyclopropylmethyl), cycloalkenyl, cycloalkenyl lower alkyl, furyl lower alkyl (e.g., furyl methyl), thiophenyl lower alkyl (e.g., thiophenyl methyl), pyridinyl lower alkyl (e.g., 2-pyridinyl methyl), piperidinyl lower alkyl (e.g., 2-piperidinyl methyl), or thiazolyl lower alkyl (e.g., 5-thiozolylmethyl);

$R_2$ and $R_3$ represent hydrogen, $\beta$-hydroxy, $\beta$-alkoxy or $\beta$-acyloxy, (e.g., lower acyloxy) wherein one is hydrogen;

$R_4$ represents hydroxy, lower alkoxy, acyloxy (e.g., lower acyloxy),

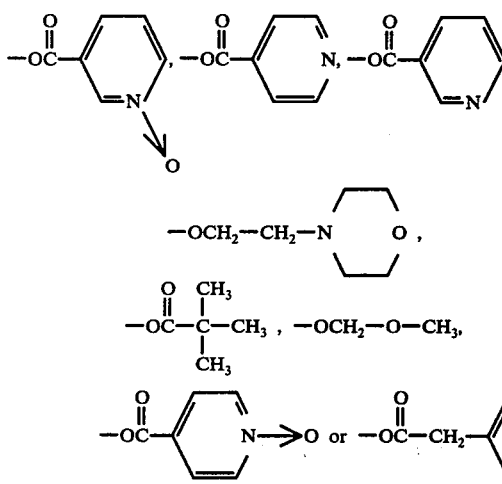

$R_5$ represents hydrogen, hydroxy or lower acyloxy; and the pharmaceutically acceptable salts thereof.

Further objects, features and advantages of the present invention will become apparent from the detailed description of preferred embodiments which follows.

DETAILED DESCRIPTION OF PREFERRED EMBODIMENTS

It has been found in accordance with the present invention that 6- and 8-keto morphine and morphinan derivatives, with or without a hydroxy group at the 14 position thereof, are readily converted to 6$\beta$-hydroxy or 8$\beta$-hydroxy compounds using formamidinesulfinic acid in alkaline solution to effectuate the stereoselective reduction at the 6-keto or 8-keto position.

The present invention provides a simple and effective process for synthesizing various 6$\beta$-hydroxy and 8$\beta$-hydroxy derivatives in the morphine and morphinan series having the following structural formulas:

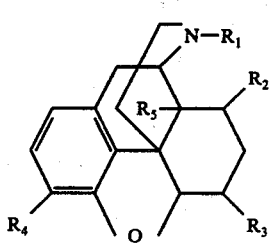

or the formula:

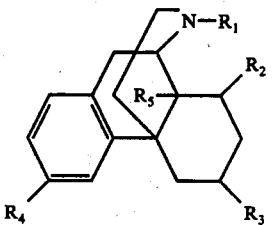

wherein $R_1$ represents hydrogen, lower alkyl (e.g., methyl, ethyl, propyl, etc.), lower alkenyl (e.g., 1-propenyl), lower alkynyl, carbocyclic lower alkyl (e.g., cyclopropyl methyl, cyclobutylmethyl, etc.), lower alkyl ring-substituted carbocyclic lower alkyl (e.g., methylcyclopropylmethyl), cycloalkenyl, cycloalkenyl lower alkyl, furyl lower alkyl (e.g., furyl methyl), thiophenyl lower alkyl (e.g., thiophenyl methyl), pyridinyl lower alkyl (e.g., 2-pyridinyl methyl), piperidinyl lower alkyl (e.g., 2-piperidinyl methyl), or thiozolyl lower alkyl (e.g., 5-thiozolylmethyl);

$R_2$ and $R_3$ represent hydrogen, $\beta$-hydroxy, $\beta$-alkoxy or $\beta$-acyloxy, (e.g., lower acyloxy, wherein one is hydrogen;

$R_4$ represents hydroxy, lower alkoxy, acyloxy (e.g., lower acyloxy),

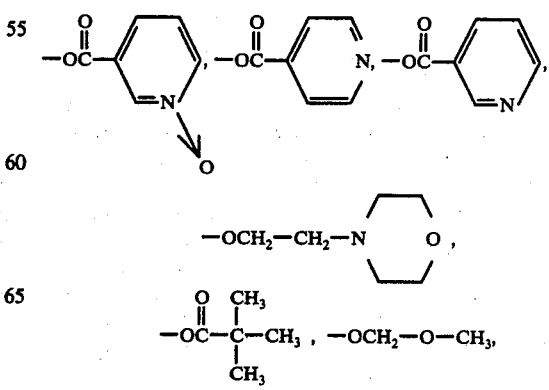

-continued

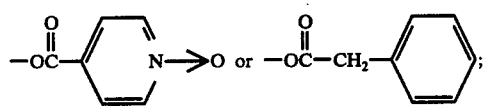

$R_5$ represents hydrogen, hydroxy or lower acyloxy; and the pharmaceutically acceptable salts thereof.

In carrying out the process according to the invention, a preferred group of starting materials are compounds having the formula:

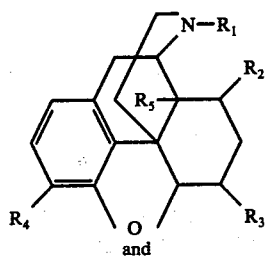
I and

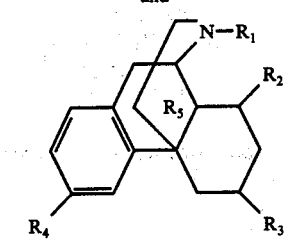
II wherein $R_1$ is selected from the group comprising hydrogen, lower alkyl (e.g., methyl, ethyl, propyl, etc.), lower alkenyl (e.g., 1-propenyl),

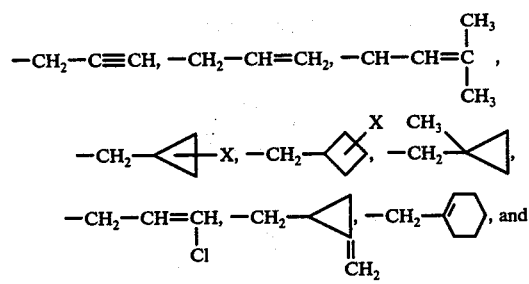

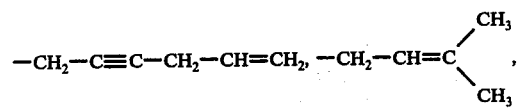

where
X is hydrogen or methyl;
$R_2$ and $R_3$ are selected from the group comprising hydrogen and =O, and =O and hydrogen, respectively;
$R_4$ is selected from the group comprising hydroxy, lower alkoxy and lower acyloxy; and
$R_5$ is selected from the group comprising hydrogen and hydroxyl.

A more preferred embodiment is the compounds of formula I or II wherein $R_1$ is hydrogen, lower alkyl, $-CH_2-C\equiv C-CH_2-CH=CH_2, -CH_2-CH=C\begin{smallmatrix}CH_3\\ \\CH_3\end{smallmatrix},$ -continued

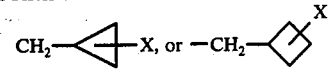

in which X is H or $CH_3$, $R_4$ is OH or $OCH_3$, and $R_5$ is H or OH or (lower) acyl.

Another more preferred embodiment is the compounds of formula I or II where $R_1$ is hydrogen, lower alkyl,

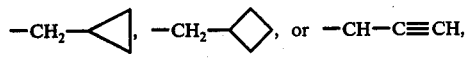

$R_4$ is OH or $OCH_3$, and $R_5$ is H or OH.

Most preferred embodiments are:
(1) The compounds of formula I or II wherein $R_4$ is OH, $R_1$ is

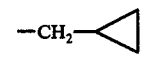

and $R_5$ is H or OH.
(2) The compounds of formula I or II wherein $R_4$ is

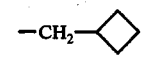

and $R_5$ is H or OH.

The new compounds provided in accordance with the invention are preferably those having the formula

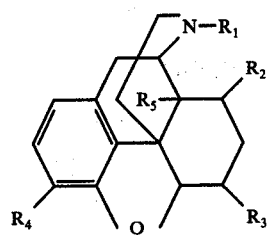
I wherein:
$R_1$ is selected from the group comprising hydrogen, lower alkyl (e.g., methyl, ethyl, propyl, etc.), lower alkenyl (e.g., 1-propenyl), $-CH_2-C\equiv CH, -CH_2-CH=CH_2, -CH-CH=C\begin{smallmatrix}CH_3\\ \\CH_3\end{smallmatrix},$

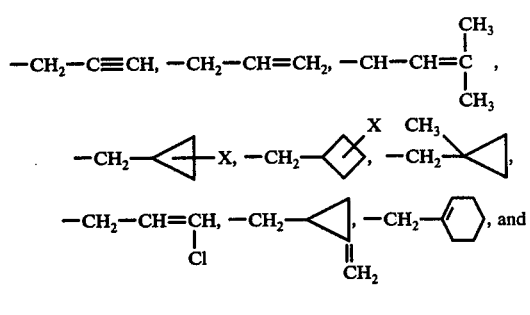

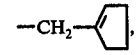

where X is hydrogen or methyl;
$R_2$ and $R_3$ are selected from the group comprising $\beta$-hydroxy, $\beta$-alkoxy and $\beta$-lower acyloxy;

$R_4$ is selected from the group comprising hydroxy, lower alkoxy, lower acyloxy,

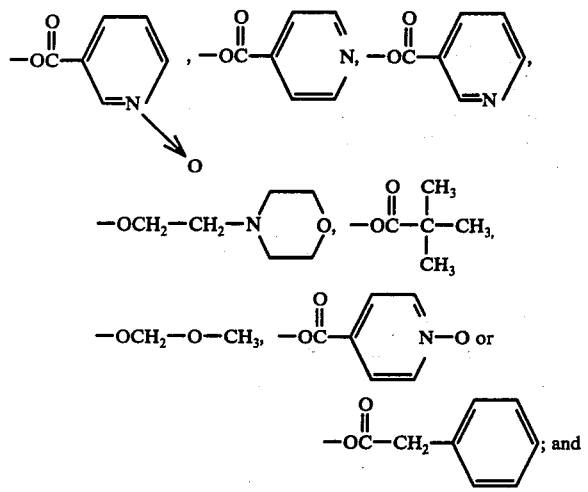

$R_5$ is selected from the group comprising hydrogen, hydroxy, and lower acyloxy; and the pharmaceutically acceptable salts thereof.

A more preferred embodiment is the compounds of formula I wherein $R_1$ is hydrogen, lower alkyl,

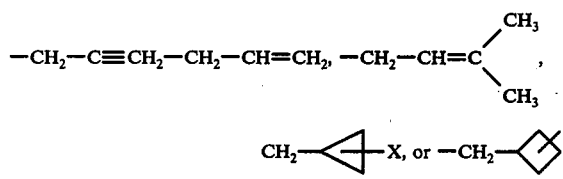

in which X is H or $CH_3$, $R_4$ is

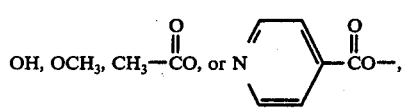

$R_2$ is hydrogen, and
$R_5$ is H, OH, a (lower) acyloxy; or a pharmaceutically acceptable acid addition salt thereof.

Another more preferred embodiment is the compounds of formula I where $R_1$ is hydrogen, lower alkyl,

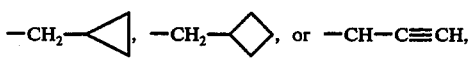

$R_2$ is hydrogen,
$R_4$ is

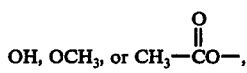

and $R_5$ is H or OH; or a pharmaceutically acceptable acid addition salt thereof.

Most preferred embodiments are:

(1) The compounds of formula I wherein $R_2$ is H, $R_1$ is

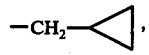

$R_4$ is OH, and
$R_5$ is OH; or the hydrochloride salt thereof.

(2) The compound of formula I wherein $R_2$ is H, $R_1$ is

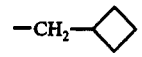

$R_4$ is OH, and $R_5$ is OH; or the hydrochloride salt thereof.

As specific compounds obtained in accordance with the present invention, there may be mentioned 6β-hydroxy-17-cyclobutylmethyl-4,5α-epoxy-3,14-dihydroxymorphinan, 6β-hydroxy 17-methyl-4,5α-epoxy-3,14-dihydroxymorphinan, 6β-hydroxy 17-methyl-4,5α-epoxy-3-hydroxymorphinan, 6β-hydroxy 17-methyl-4,5α-epoxy-3-methoxymorphinan and 8β-hydroxy dihydropseudo codeine which are directly obtained by the formamidinesulfinic acid reduction of the corresponding 6-keto and 8-keto starting materials.

The starting materials according to the present invention are either readily available or can be readily produced. For example, the morphine derivatives are well known according to the literature, as described, for example, in the introduction hereto, and many are commercially available. Similarly, the pseudocodeine series of compounds is well known, and the analogues to the morphine compounds can be prepared in accordance with analogous procedures.

The morphinan compounds of the instant invention have the basic nucleus which is numbered and represented by the following plane formula:

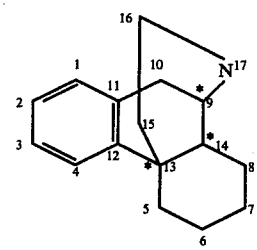

Although there are three asymmetric carbons (asterisks) in the morphinan molecule, only two diastereoisomeric (racemic) forms are possible, because the iminoethano system, attached to position 9 and 13, is geometrically contained to a cis-(1,3-diaxial)-fusion. These racemates can therefore differ only at the junction of rings B and C - in other words, in the configuration of carbon 14. The only variable will be the cis and trans relationship between the 5 (13) and 8 (14) bonds (Analgetics, Ed. George de Stevens, Academic Press, New York, p. 137 (1965).

When in the compounds of the present invention, the 5 (13) and 8 (14) bonds are trans to each other, we have compounds commonly designated as "isomorphinans." On the other hand, when 5 (13) and 8 (14) are cis to each other, we have compounds commonly designated as "morphinans." The use of a graphic representation of a "morphinan" or "isomorphinan" is meant to include the dl racemic mixture and the resolved d and l isomers thereof.

The "isomorphinans" disclosed and claimed herein are primarily useful as intermediates in the preparation of the biologically potent analgetic and/or narcotic antagonist agent of the present invention.

In addition, the "isomorphinan" and "morphinan" compounds of the present invention can exist as two optical isomers, the levorotatory and dextrorotatory isomers. The optical isomers can be graphically illustrated as:

MORPHINANS

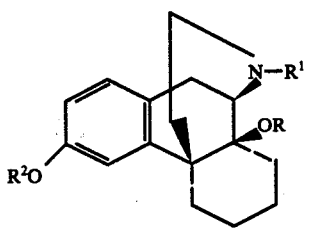

and

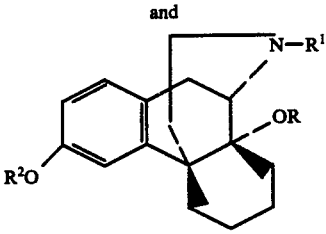

ISOMORPHINANS

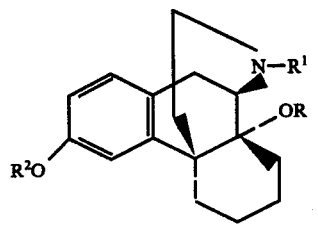

and

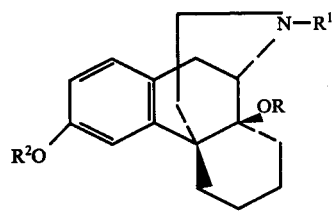

The present invention embodies all of the isomorphinan and morphinan isomers including the optical isomers in their resolved form. These isomers which do not possess the desired biological activity can be transformed chemically into the desired product.

The optical isomers can be separated and isolated by fractional crystallization of the diastereoisomeric salts formed, for instance, with d- and l-tartaric acid or D-(+)-α-bromocamphor sulfonic acid. The levorotatory isomers of the compounds of the present invention are the most preferred embodiments.

For the purpose of this disclosure, the term "(lower) alkyl" is defined as an alkyl radical containing 1 to 6 carbon atoms. "(Lower) alkenyl" is defined as a hydrocarbon radical of 3 to 7 carbons containing one double bond. The term "(lower) acyl" is an acyl radical of 2 to 6 carbon atoms, e.g., acetyl, propionyl, isobutyryl, etc.

6-oxygenated derivatives of morphinans have previously been synthesized, for example as described by Sawa et al., in Japanese Pat. No. 7104,168. As an example of the preparation of N-substituted derivatives, the intermediate nor-compound (I) prepared by Sawa above may be reacted with cyclobutylcarbonylchloride to give the amide $(IIa)$. Reduction of the amide with borane gives 3,6,14-trihydroxy-N-cyclobutylmorphinan$(II)$. The latter compound may be oxidized to the 6-keto compound$(III)$. Alternatively, the 6-keto compound$(III)$ may be prepared from (I) by making the ethylene ketal of (I), followed by acylation with cyclobutylcarboxylchloride followed by borohydride reduction.

This is illustrated by the following reaction sequences. It is advantageous in these sequences to protect the phenolic OH by methylation, the methyl group being removed at the end with pyridine hydrochloride. The protected nor-compound may be alkylated directly with cyclobutylmethylbromide to give 6-ketobutorphanol.

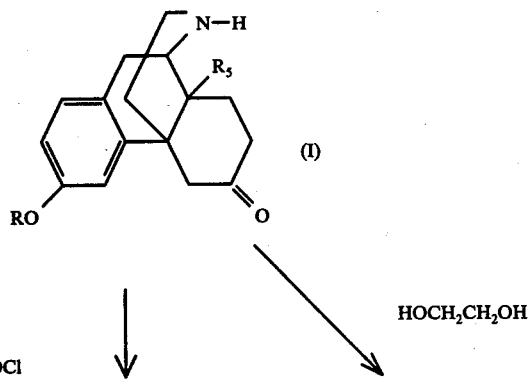

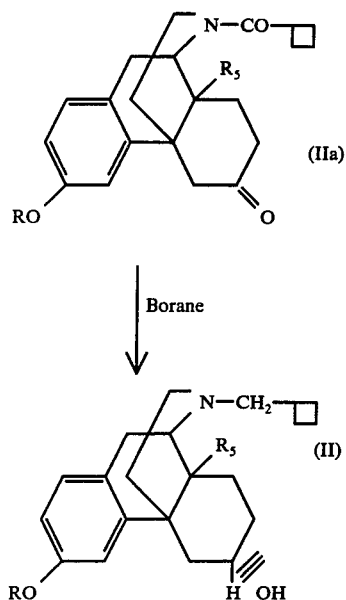

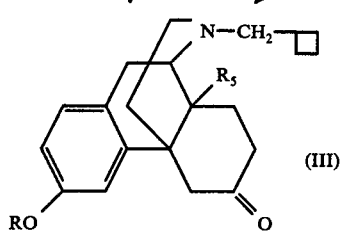

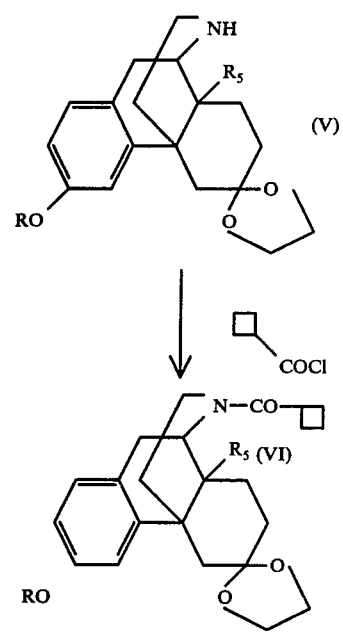

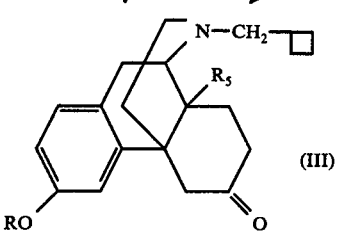

One of the distinct advantages of the present invention is that preferably the formamidinesulfinic acid reducing agent of the invention can be introduced into the reaction system in the form of an aqueous alkaline solution thereof thus obviating the necessity of using organic solvents which often are unsuitable for oxymorphone derivatives due to the insolubility of such compounds in organic solvents. Morphine and morphinan derivatives having a phenolic group thereon dissolve in, for example, an aqueous sodium hydroxide solution of formamidinesulfinic acid and are thus amenable to direct reduction with formamidinesulfinic acid. However, due to variations in the solubility of certain of the starting materials employed herein, it may be desirable to employ alkaline solutions of the formamidinesulfinic acid in other solvents or mixtures thereof. For instance, dihydroisocodeinone is only slightly soluble in water and its reduction may be carried out utilizing formamidinesulfinic acid in an aqueous-ethanol mixture.

Since the phenolic hydroxyl groups of morphine compounds are generally convertible to their methyl ethers forming compounds in the codeine series, the process of the invention is advantageously applicable to the synthesis of various compounds of the isocodeine and pseudocodeine series, either by reduction of morphine derivatives and subsequent conversion to codeine derivatives or by direct reduction of 6-keto or 8-keto codeine derivatives. Accordingly, the present process obviates the necessity of both an epimerization step and the separation of products which result from the hydrolysis of β-chlorocodide or bromocodide which are alternate synthetic pathways for obtaining isocodeine derivatives.

Upon obtaining 6β-hydroxy and 8β-hydroxy compounds in accordance with the present invention, the hydroxy group may then be readily reacted with, for example, diazoalkanes or acid anhydrides to obtain the corresponding alkoxy and acyloxy derivatives.

The concentration of formamidinesulfinic acid reducing agent generally comprises a three to four molar excess compared to the concentration of the starting material. Of course, certain morphine and morphinan starting materials may require that the concentration of formamidinesulfinic acid be adjusted to compensate for steric hindrance and solubility characteristics of the starting material which may affect the reduceability of the 6-keto or 8-keto reactant.

The concentration of base in the alkaline solution of the reducing agent is sufficiently high to obtain a highly alkaline solution, e.g., up to about pH = 13 or higher. The basicity of the reducing solution may also be adjusted by the addition of, for example, minor amounts of hydrochloric acid and suitable buffering agents (e.g., bicarbonatecarbonate buffer) to obtain the final desired pH range.

Definite evidence for the assignment of 6β-hydroxy and 8β-hydroxy orientation and determination of stereoselective reduction are obtained from the proton nuclear magnetic resonance spectrum of the various compounds obtained in accordance with the process of the invention. For example, the spectrum exhibits a doublet centered at about 4.54 (J=6Hz) due to the 5β proton and a multiplet due to the 6α proton in the region γ 3.68–3.45. As an example of the effectiveness of the process of the invention, it permits the preparation of pure 6β-epimeric alcohols from 6-keto derivatives in yields of 40% and higher.

In certain of the non-limiting examples of preferred embodiments of the invention which follow, melting points are determined on a Thomas-Hoover apparatus without correction. Infra red spectra are obtained on a Perkin-Elmer 257 grating infrared spectrophotometer. Mass spectra are obtained on a Varian M-66 double-focusing cycloidal pass mass spectrometer. Proton nuclear spectra are recorded on a Varian XL-100 spectrometer ($Me_4Si$), using $CDCl_3$ as the solvent. Thin-layer chromatography is performed on Analtech silica gel plates using a solvent system of methylacetate-hexane-ethanol-ammonia (60:25:14:1) utilizing Dragendorff's solution for visualization.

EXAMPLE 1

A solution of 754 mg. (2 mmol.) of 17-cyclopropyl-methyl-4,5α-epoxy-3,14-dihydroxymorphinan-6-one hydrochloride (naltrexone hydrochloride-Endo Laboratories, Inc., Garden City, N.Y.) in water (50 ml.) is treated with the minimum of sodium hydroxide solution (640 mg. in 50 ml. of water) until the mixture turns alkaline. The alkaline mixture is treated with 864 mg. (8 mmol.) of formamidinesulfinic acid dissolved in the remaining aqueous sodium hydroxide solution. The reaction mixture is stirred magnetically on a water bath under a current of $N_2$ at 80°–85° C. After one hour, the reaction mixture is allowed to cool and the pH adjusted to about 9.8 by the addition of a few drops of 6NHCl solution and a bicarbonate-carbonate buffer. A white precipitate is obtained and filtered, washed with cold water and allowed to dry in a vacuum desiccator over sodium hydroxide.

The 6β-hydroxy product obtained weighs 607 mg. (88.5%); mp 188°–190° C., TLC $R_f$ 0.55; NMR 4.54 (d, 1, J=6 Hz, 5β-H), 3.68–3.45 (m, 1, 6α-H).

The product is converted into its hydrochloride by dissolution in an equal volume of EtOH and $CH_3COCH_3$ and treating with 6 N HCl. Recrystallization (95% EtOH-$CH_3COCH_3$) gives crystals of the hydrochloride of the product mp 205°–210° dec; ir (KBr disk) 3500–3100$cm^{-1}$ (broad); $[\alpha]^{25}D$-133.8° (c 1, $H_2O$); mass spectrum (70 eV)m/e 343 (100%). Anal. ($C_{20}H_{26}ClNO_4 \cdot H_2O$) C, H, N, Cl.

EXAMPLE 2

A solution of 1,48 g. (4 mmol.) of 17-allyl-4,5α-epoxy-3,14-dihydroxymorphinan-6-one hydrochloride (Naloxone hydrochloride - Endo Laboratories, Inc., Garden City, N.Y.) in the minimum volume of $H_2O$ is treated with part of a solution of aqueous NaOH (2.22 g. in 130 ml. of $H_2O$) until the mixture turns clear and alkaline. Formamidinesulfinic acid (1.85 g., 10 mmol.) is dissolved in the remaining NaOH solution and is added to the reaction mixture. The final aqueous volume is made up to 200 ml. Experimental conditions are as in Example 1; however, a 3 hour period is necessary for reaction to go to completion. On work-up, a white precipitate is obtained. This, on drying, weighs 0.52 g. (40%); mp 107°–110°; TLC $R_f$ 0.70; NMR 4.52 (d, 1, J=6 Hz, 5 —H), 3.68–3.40 (M, 1, 6 —H), 5.94–5.60 (m, 1, vinylic H), 5.26–5.10 (t, 2, gem vinylic H). The 6β-product is converted to its hydrochloride and is recrystallized (95% EtOH—$CH_3COCH_3$): mp of hydrochloride 205°–207° dec; $[\alpha]^{25}D$-158.3° (c 0.7, $H_2O$); mass spectrum (70 eV) m/e 329 (100%). Anal. ($C_{19}H_{24}ClNO_4 \cdot H_2O$) C, H, N, Cl.

EXAMPLE 3

6β-hydroxy 17-cyclobutyl-methyl-4,5α-epoxy-3,14-dihydroxy-morphinan is obtained from the corresponding 6-keto starting material in the same manner as in Example 1.

EXAMPLE 4

75 mg. (0.25 mmol.) of 17-methyl-4,5α-epoxy-3-methoxymorphinan-6-one is dissolved in 20 ml. of methanol. The resulting solution is treated with 10 ml. of aqueous sodium hydroxide (150 mg.) containing 95 mg. (0.88 mmol.) formamidinesulfinic acid. The resulting mixture is magnetically stirred for one hour at 80° C. under a current of $N_2$. The reaction mixture is thereafter stripped of ethanol and extracted with chloroform. Upon evaporation of chloroform, a residue of dihydroisocodeine is obtained. The NMR spectrum ($CDCl_3$) of the dihydroisocodeine product is identical with that of the published reference spectrum (see S. Okuda et al., Chem. Pharm. Bull., 12, 104 (1964). The dihydroisocodeine free base is converted to its hydrochloride which has no melting point below 300° C.

EXAMPLE 5

The procedure of Example 4 is repeated except that 0.25 mmol. of dihydropseudo codeinone (8-keto compound) is used in place of the corresponding 6-keto compound, and ethanol is utilized as the organic solvent instead of methanol. The 8β-hydroxy reduction product is recovered from this reaction.

EXAMPLE 6

In an anhydrous system 32 g of 3-methoxy-14-hydroxy-6-ketomorphinan, 16 ml triethylamine and 300 ml of benzene are stirred together and, over a 30 minute period, a solution of 13 g of cyclobutylcarbonylchloride in 100 ml of benzene is added. The internal temperature is kept below 25° by means of an ice bath, after which stirring is continued for four more hours at room temperature. In the isolation, triethylaminehydrochloride is removed by filtration, the solvent evaporated, and the residue solidified by stirring in 200 ml of petroleum ether to give crude N-cyclobutylcarbonyl-3-methoxy-14-hydroxy-6-ketomorphinan.

A solution of 4.5 g of borane in 300 ml of tetrahydrofuran (THF) is cooled to −5° under a stream of nitrogen, and then a solution of 35 g of N-cyclobutylcarbonyl-3-methoxy-14-hydroxy-6-ketomorphinan in 200 ml of THF is added slowly over a 45 minute period, keeping the reaction temperature below 0° C. The reaction mixture is then refluxed for 3 hours, cooled, and 150 ml of ZN HCl is added slowly, which induces a vigorous evolution of gas. The solution is then evaporated to a volume of 150 ml in vacuo, diluted with 200 ml of water, and the pH adjusted to 9.0 by the careful addition of 14 N ammonium hydroxide. The precipitate is stirred for two hours and filtered to give crude N-cyclobutyl-methyl-3-methoxy-6α,14β-di-hydroxymorphinan.

One gram of potassium metal is reacted with t-butyl alcohol in anhydrous benzene to give potassium-t-butoxide. This suspension is heated with 2.5 g of N-cyclobutylmethyl-3-methoxy-6$\beta$,14$\beta$-dihydroxy-morphinan and 16 g of benzophenone under reflux for 3 hours. The reaction mixture is then extracted with three 20 ml portions of 2N hydrochloric acid, the combined acid extracts are made alkaline to a pH of 9.0, re-extracted with chloroform, and the solvent removed, after drying, in vacuo. The product is extracted from the insolubles with ether, and then the methoxy group is removed as follows to give N-cyclobutylmethyl-3,14$\beta$-dihydroxy-6-ketomorphinan: 15 g of the methoxy compound and 30 g of pyridine hydrochloride are heated together under a $N_2$ atmosphere at 190°–196° C. for 4 hours, and the pyridine is distilled off during the heating period. After cooling to room temperature, 25 ml of water is added and the mixture is poured into an additional 100 ml. cold water. The pH is adjusted to 11.5 with 20% aqueous NaOH with cooling and insoluble material filtered off. The pH of the filtrate is then adjusted to 8.5–9.0 with HCl and stirred for 4 hours until crystallization occurs. The product is filtered off and recrystallized from acetone-methanol.

This compound is treated in accordance with the procedure described in Example 1 to yield N-cyclobutylmethyl-3,6$\beta$,14$\beta$-trihydroxy morphinan.

EXAMPLE 7

A mixture of 20 g of 3-methoxy-14-hydroxy-6-ketomorphinan, 15 g of p. toluene sulfonic acid, 22 g of ethyleneglycol and 200 ml of benzene are heated slowly on a steam bath, and then refluxed with a condenser equipped for water separation until no more water comes off. The solution is poured into 500 ml of water and the pH is adjusted to 10.0 with 30% aqueous NaOH. The precipitate is collected, washed with methanol and dried to give 3-methoxy-14-hydroxy-morphinan-6-cyclic ethyleneketal.

A solution of 10 g of the ketal is treated with 10 g of cyclobutylcarbonylchloride in 200 ml of methylenechloride and 40 g of triethylamine are added over a period of one hour. The solution is then refluxed for 6 hours and then the triethylamine hydrochloride is filtered off. The methylenechloride is distilled off in vacuo. The residue is recrystallized from methanol to give N-cyclobutylcarbonyl-3-methoxy-14-hydroxy-morphinan-6-cyclic ethyleneketal.

A stirred suspension of 5 g of lithium aluminum hydride in 1000 ml of THF is treated slowly with a suspension of 6 gms of N-cyclobutylcarbonyl-3-methoxy-14-hydroxymorphinan-6-cyclic ethyleneketal. After treatment the mixture is heated on a steam bath with stirring for 3 hours. After standing overnight, the excess $LiAlH_4$ is decomposed by the slow addition of 100 ml of ethylacetate over a one hour period. The reaction mixture is then poured over 100 gms of chopped ice, 200 ml of 30% NaOH is added, and the aqueous phase is extracted with chloroform. The chloroform is taken by dryness, the residue is taken up in methanol and decolorized with charcoal. The methanol is treated with an equal volume of acetone, and then the solution concentrated to crystallize the product, N-cyclobutylmethyl-3-methoxy-14-hydroxymorphinan-6-cyclic ethyleneketal.

Six grams of N-cyclobutylmethyl-3-methoxy-14-hydroxy-morphinan-6-cyclic ethyleneketal are hydrolyzed by dissolving the acetal in 25 ml of 15% aqueous HCl, heating on a steam bath for 2 hours, decolorizing with charcoal and then adjusting the solution to pH 11 with 30% NaOH in water. The solid obtained is recrystallized from methanol to give N-cyclobutyl-methyl-3-methoxy-14$\beta$-dihydroxy-6-ketomorphinan. The methoxyl group is removed as described in Example 6 to give N-cyclobutylmethyl-3,14$\beta$-dihydroxy-6-ketomorphinan. This product is then further reacted with formamidinesulfinic acid as in Example 6 to give the 6$\beta$-hydroxy product.

EXAMPLE 8

A mixture of 0.5 g of N-cyclobutylmethyl-3,6$\beta$,14$\beta$-trihydroxy morphinan and 15 ml of nicotinoyl chloride in 20 ml of dry pyridine is allowed to stand overnight. After brief warming on a steam bath, the solution is quenched with water, neutralized with sodium carbonate solution and extracted with benzene to give N-cyclobutylmethyl-3,6-nicotinoyloxy-14$\beta$-hydroxymorphinan.

EXAMPLE 9

A mixture of 0.5 g of N-cyclobutylmethyl-3,6$\beta$,14$\beta$-trihydroxy-morphinan and 15 ml of acetic anhydride in 10 ml of glacial acetic acid are allowed to stand overnight and then worked up as described in Example 8 to give N-cyclobutylmethyl-3,6-acetoxy-14$\beta$-hydroxymorphinan.

EXAMPLE 10

A solution of 0.5 g of N-cyclobutylmethyl-3,6$\beta$,14$\beta$-trihydroxy morphinan in methylcellosolve is converted to the sodium salt with 0.1 g of sodium hydride or sodium methoxide, and then reacted with 0.5 g of bromomethylether in benzene. After work-up as described in Example 11 one obtains N-cyclobutylmethyl-3,6-methoxymethyl-14$\beta$-hydroxy-morphinan.

PHARMACOLOGICAL EVALUATION

The results of pharmacologic evaluation in mice of 6$\beta$-hydroxy-17-cyclopropylmethyl-4,5$\alpha$-epoxy-3,14, dihydroxymorphinan and 6$\beta$-hydroxy-17-cyclobutyl-methyl-4,5$\alpha$-epoxy-3, 14,dihydroxymorphinan obtained in accordance with the present invention are set forth below. Narcotic antagonist activity is measured by the method of Blumberg and Dayton (Adv. Biochem. Psychopharmacol., 8, 33, (1973)). Antinociceptive activity is determined by the use of the phenylquinone writhing test (H. Blumberg et al., Proc. Soc. Exp. Biol. Med., 118, 763 (1965).

The cyclopropylmethyl compound has an $ED_{50}$ in the writhing test of about 10 mg/kg (subcutaneous) and an $ED_{50}$ of about 0.75 mg/kg (subcutaneous) in the antagonist test and the activity of the compound is thus comparable of that of cyclazocine with respect to antagonist activity with little or no clinically significant agonist activity. The cyclobutylmethyl derivative shows an $ED_{50}$ of about 2.6 mg/kg in the writhing test and an $ED_{50}$ of about 2.8 mg/kg in the antagonist test. The cyclobutylmethyl compound, accordingly is observed to be approximately as potent as pentazocine as an agonist and more potent than the same compound with respect to antagonist activity but less active than, for instance, naloxone (antagonist $ED_{50}=0.071$ mg/kg).

While the invention has been described and illustrated with reference to certain preferred embodiments thereof, those skilled in the art will appreciate that various changes, modifications and substitutions therein can be made without departing from the spirit of the inven-

What is claimed is:

1. Process for the stereoselective reduction of of 6- or 8-keto-6,7-dihydromorphine and 6- or 8-keto morphinan derivatives to form the corresponding 6β-hydroxy or 8β-hydroxy epimers thereof which comprises reducing said 6-keto or 8-keto derivatives with an alkaline solution of formamidinesulfinic acid.

2. The process of claim 1, wherein the solvent of said alkaline solution of formamidinesulfinic acid comprises water.

3. The process of claim 1, wherein said alkaline solution of formamidinesulfinic acid comprises said acid in an aqueous-ethanol solvent mixture.

4. The process of claim 1, wherein said process is carried out in an inert nitrogen atmosphere.

5. The process of claim 1, wherein said 6- or 8-keto derivatives have the formula:

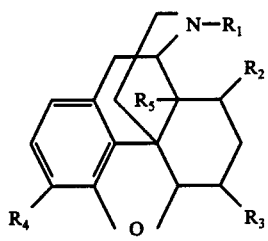

or the formula:

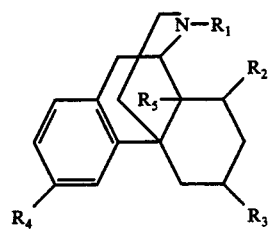

wherein $R_1$ is selected from hydrogen, lower alkyl, lower alkenyl, lower alkynyl, carbocyclic lower alkyl, lower alkyl ring-substituted carbocyclic lower alkyl, cycloalkenyl, cycloalkenyl lower alkyl, furyl lower alkyl, thiophenyl lower alkyl, pyridinyl lower alkyl, piperidinyl lower alkyl, and thiozolyl lower alkyl;

$R_2$ and $R_3$ is selected from hydrogen and =O, and =O and hydrogen, respectively;

$R_4$ is selected from hydroxy, and lower alkoxy; and $R_5$ is selected from hydrogen, hydroxy and lower acyl.

6. The process of claim 5, wherein $R_1$ is selected from hydrogen, lower alkyl,

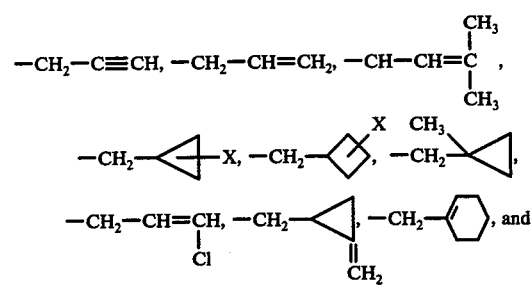

where X is hydrogen or methyl;

$R_2$ and $R_3$ are selected from hydrogen and =O, and =O and hydrogen, respectively;

$R_5$ is selected from hydrogen and hydroxyl.

7. The process of claim 6, wherein $R_1$ is selected from hydrogen, lower alkyl,

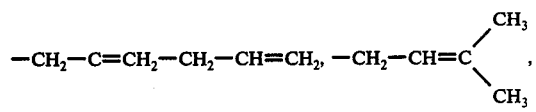

in which X is H or $CH_3$, $R_4$ is selected from

OH and $OCH_3$, and $R_5$ is selected from H, OH and (lower) acyl.

8. The process of claim 7, wherein $R_1$ is selected from hydrogen, lower alkyl,

$R_4$ is OH or $OCH_3$, and
$R_5$ is H or OH.

9. The process of claim 8, wherein $R_4$ is OH, $R_1$ is

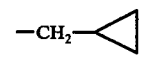

and $R_5$ is H or OH.

10. The process of claim 8, wherein $R_4$ is OH and $R_1$ is

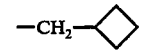

and $R_5$ is H or OH.

11. The process of claim 5, wherein a 6-keto derivative is reduced.

12. The process of claim 5, wherein an 8-keto derivative is reduced.

13. The process of claim 11, wherein a 6-keto morphine derivative is reduced.

14. The process of claim 13, wherein said derivative is selected from the group 17-cyclobutylmethyl-4,5α-epoxy-3,14-dihydroxymorphinan-6-one, 17-methyl-4,5α-epoxy-3,14-dihydroxymorphinan-6-one, 17-methyl-4,5α-epoxy-3-hydroxymorphinan-6-one, 17-methyl-4,5α-epoxy-3-methoxymorphinan-6-one.

15. The process of claim 12, wherein said derivative is dihydropseudo codeinone.

16. The process of claim 11, wherein a 6-keto morphinan derivative is reduced.

17. The process of claim 16, wherein said derivative is selected from 17-cyclobutylmethyl-3,14-dihydroxymorphinan-6-one and 17-cyclobutylmethyl-3-methoxy-14-hydroxymorphinan-6-one.

18. A compound of the formula:
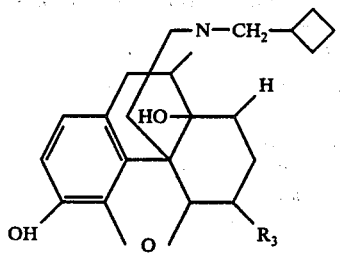
wherein:
R₃ represents β-hydroxy, lower alkoxy containing 1 to 6 carbon atoms or lower alkanoyloxy containing 2 to 6 carbon atoms, or a pharmaceutically acceptable acid addition salt thereof.
* * * * *